United States Patent [19]

Carter

[11] Patent Number: 5,686,045

[45] Date of Patent: Nov. 11, 1997

[54] METHOD FOR THE HEAT INDEPENDENT STERILIZATION OF MICROBIALLY CONTAMINATED INSTRUMENTS

[76] Inventor: Stephen D. Carter, 1895 Chartwell Trace, Stone Mountain, Ga. 30083

[21] Appl. No.: 425,855

[22] Filed: Apr. 19, 1995

Related U.S. Application Data

[63] Continuation-in-part of Ser. No. 193,731, Feb. 9, 1994, abandoned.

[51] Int. Cl.$^6$ ............................................. A61L 2/00
[52] U.S. Cl. ........................... 422/20; 422/28; 422/33
[58] Field of Search ........................ 422/20, 33, 292, 422/295, 297, 300, 28, 128; 134/1, 184; 366/127

[56] References Cited

U.S. PATENT DOCUMENTS

| | | | |
|---|---|---|---|
| 1,711,097 | 4/1929 | Kratzer | 422/39 |
| 1,728,333 | 9/1929 | Crowther | 422/39 |
| 1,728,334 | 9/1929 | Crowther | 422/39 |
| 3,007,478 | 11/1961 | Leonhardt et al. | 422/20 |
| 3,415,613 | 12/1968 | Wallden | 422/295 |
| 3,617,178 | 11/1971 | Clouston | 422/33 |
| 3,627,209 | 12/1971 | Scott | 239/533 |
| 3,708,263 | 1/1973 | Boucher | 422/30 |
| 3,913,614 | 10/1975 | Speck | 137/543.19 |
| 3,944,387 | 3/1976 | Schreckendgust | 422/295 |
| 4,193,818 | 3/1980 | Young et al. | 422/20 |
| 4,226,642 | 10/1980 | Baran | 134/10 |
| 4,241,010 | 12/1980 | Baran | 422/2 |
| 4,543,987 | 10/1985 | Ekeleme, Jr. et al. | 137/540 |
| 4,748,003 | 5/1988 | Riley | 422/112 |
| 4,944,919 | 7/1990 | Powell | 422/26 |
| 4,973,449 | 11/1990 | Kolstad et al. | 422/27 |
| 5,049,400 | 9/1991 | Hayden | 422/20 |
| 5,120,512 | 6/1992 | Masuda | 422/297 |
| 5,288,462 | 2/1994 | Carter et al. | 422/39 |
| 5,377,709 | 1/1995 | Shibano | 134/184 |
| 5,447,171 | 9/1995 | Shibano | 134/184 |

FOREIGN PATENT DOCUMENTS

| | | | |
|---|---|---|---|
| 40887 | 12/1981 | European Pat. Off. | 422/39 |
| 3445990 | 6/1986 | Germany | 422/39 |
| 0366498 | 9/1962 | Switzerland | 134/1 |
| 00947699 | 1/1964 | United Kingdom | 422/20 |
| 2190993 | 12/1987 | United Kingdom | 137/535 |

OTHER PUBLICATIONS

Boucher, R.M.G. "Ultrasonics–A Tool To Improve Biocidal ..." Canadian Journal of Pharmaceutical Sciences, vol. 14, No. 1, pp. 1–12, 1979.

(List continued on next page.)

*Primary Examiner*—Robert J. Warden
*Assistant Examiner*—Krisanne M. Thornton
*Attorney, Agent, or Firm*—Bell, Seltzer, Park & Gibson

[57] ABSTRACT

Methods for sterilizing an instrument contaminated with biological matter are disclosed. The apparatus generally includes a container for containing a room temperature antimicrobial solution and a lid that can seal the container such that a gas is trapped within the container and above the antimicrobial solution. The apparatus provides a pressure, independent of heat, within the sealed container to greater than one atmosphere. Vibration is also provided to vibrate the container, and its contents, such that biological matter on the instruments is removed and all microbes on the instrument are exposed to the antimicrobial solution. The pressure drives and forces the antimicrobial solution into the cracks and crevices of the instrument and also into the outer membrane of the microbe, which can be first softened or attenuated by the vibrations. The method of sterilization generally includes submerging the instrument in the room temperature antimicrobial solution, sealing the container to trap a gas above the antimicrobial solution, increasing the pressure, independent of heat, within the container to force the antimicrobial solution into the cracks and crevices of the instrument and into contact with the microbe(s), and vibrating the container to remove matter from the instrument and to soften the outer membrane of the microbe.

12 Claims, 1 Drawing Sheet

OTHER PUBLICATIONS

Sanchez et al. "Decontaminating Dental Instruments..." Clinical Practice, JADA, vol. 126, Mar. 1995, pp. 359–368.

Spach et al. "Transmission of Infection by Gastrointestinal Endoscopy and Bronchoscopy" American College of Physicians, 1993.

Hanson et al. "A Study of Glutaraldehyde Disinfection of Fibreoptic Bronchoscopes..." The Hospital Infection Society, 1992.

Epstein et al. "Rotary Dental Instruments and Potential Risk of..." JADA, vol. 124, Dec., 1993.

Epstein et al. "Assessing Viral Retention..." JADA, vol. 126, Jan., 1995.

METHOD FOR THE HEAT INDEPENDENT STERILIZATION OF MICROBIALLY CONTAMINATED INSTRUMENTS

This application is a Continuation-In-Part of U.S. application Ser. No. 08/193,731, filed Feb. 9, 1994 and now abandoned.

FIELD OF THE INVENTION

This invention is drawn to an apparatus and method for sterilizing a microbially contaminated instrument by submerging a contaminated instrument in an antimicrobial solution in a container, closing the container and increasing the pressure within the container such that the antimicrobial solution is forced into the cracks and microscopic crevices of the instrument, and/or into the outer membrane of the microbe to thereby neutralize the microbe and sterilize the instrument. The apparatus and method are particularly suited to sterilize fragile, delicate and heat sensitive dental and medical instruments. A vibration means is also provided that vibrates the container, and its contents, such that biological matter on the instruments is removed and all microbes on the instrument are exposed to the antimicrobial solution.

BACKGROUND OF THE INVENTION

Infection control is essential to medical and dental practices. Indeed, the Center for Disease Control, medical associations, dental associations and various states are passing laws and guidelines to increase the infection control measures that must be taken by dentists and physicians. In particular, concerns over the patient to patient or staff to patient transfer of various diseases such as hepatitis B virus, HIV and other diseases have been on the rise. It is believed that most disease transfer is primarily due to the continual reuse of instruments. Therefore, efforts to combat disease transfer have generally focused on sterilizing instruments through the use of one or more of six sterilants: steam, chemical vapor, dry heat, chlorine dioxide, ethyl oxide, glutaraldehyde-containing liquid, and formaldehyde. McErlene et al., *Assessment of the Effectiveness of Dental Sterilizers Using Biological Monitors,* J.Can. Dent. Assoc. 58(6): 481–83(1992); B. Nystrom, *New Technology for Sterilization and Disinfection,* Amer. Jrl. of Med. 91(3B) 2645–2665 (1991). However, the above-listed sterilants, alone and in combination, often fail to adequately, and space and cost effectively, provide a safe means for sterilization. McErlene et al., *Assessment of the Effectiveness of Dental Sterilizers Using Biological Monitors,* J.Can. Dent. Assoc. 58(6): 481–83(1992); B. Nystrom, *New Technology for Sterilization and Disinfection,* Amer. Jrl. of Med. 91(3B): 2645–65(1991); and N. Skaug, *Proper Monitoring of Sterilization Procedures Used in Oral Surgery,* Int. J. Oral Surg. 12: 153–58(1983).

The high percentage of sterilization ineffectiveness was highlighted in one alarming study that showed that 33% of the autoclaves used in general dental practice did not inactivate microbes. Simonsen et al., *An Evaluation of Sterilization by Autoclave in Dental Offices,* J.Dent. Res. 58(A): Abstract No. 1236(1979). And, in an even more alarming study of instrument sterilization procedures in oral surgery clinics, 23% of steam autoclaves; 50% of dry-heat oven sterilizers; and 100% of gas autoclaves did not kill biological spores. N. Skaug, *Proper Monitoring of Sterilization Procedures Used in Oral Surgery,* Int. J. Oral Surg. 12: 153–58(1983).

Moreover, several other recent studies have shown that autoclave and heat sterilization routinely do not sterilize instruments. See Palenik, *Effects a Steam Sterilization on the Contents of Sharps Containers,* Am.J.Infect. Control, 21(1): 28–33 (February 1993); Palenik et al., *Effectiveness of Steam Sterilization on the Contents of Sharps Containers,* Clin. Prev. Dent., 14(1): 28–34(January–February 1992); B. Nystrom, *New Technology for Sterilization and Disinfection,* Am. J. Med., 91(3B): 264S–266S (Sep. 16, 1991); and Palenik et al., *Effectiveness of Steam Autoclaving on Bacterial Endospores Placed Within Five Types of Sharp Containers Was Tested,* Am.J.Dent 3(6): 239–44(December 1990). Other recent studies have shown that hard to reach areas of dental and medical instruments are not adequately decontaminated by various combinations of presoaking agents, dishwashers, ultrasonic cleaners, detergents and water. E. Sanchez & G. MacDonald, *Decontaminating Dental Instruments: Testing the Effectiveness of Selected Method,* JADA 126:359–68(March, 1995). In fact, the effective sterilization of many instruments has been so unreliable that instruments are being redesigned to facilitate effective cleaning and disinfection. Spach et al., *Transmission of Infection By Gastrointestinal Endoscopy and Bronchoscopy,* Annals of Internal Medicine 118: 117–28(1993).

The effectiveness of instrument sterilization is typically influenced by many factors: the types of instruments in the load, the bulk of the load to be sterilized, the packaging materials used, the arrangement of the load, the sterilizing solution used, and the operation of the sterilizer and its effectiveness.

Another problem commonly associated with sterilization techniques such as autoclaves and heat killing is that often biological matter from the patient remains on the instrument such that the microbes are insulated from the sterilization attempts. For example, the serrations, hinges and holes of many instruments effectively hide microbes from sterilization. Thus, problems are caused by the sterilization methods inability to sterilize the entire instrument.

In addition to inadequate sterilization equipment, problems with sterilization methods also occur because of human error. Moreover, the expense and cost of safe effective sterilization techniques may force the use of smaller and cheaper sterilization techniques that are not effective.

A need therefore exists for an apparatus and method for sterilizing dental and medical instruments that is quiet, convenient, easy to use, and inexpensive.

A need also exists for an apparatus and method for sterilizing dental and medical instruments that completely sterilizes the contaminated instrument.

A need further exists for an apparatus and method for sterilizing dental and medical instruments that neutralizes a contaminating microbe by forcing an antimicrobial into contact with the microbe.

A need also exists for an apparatus and method of sterilizing a dental and medical instrument that removes biological matter from a contaminated instrument such that after the biological matter is removed, more microbes are exposed to the antimicrobial solution and the instrument is completely sterilized.

A need also exists for an apparatus and method of sterilizing instruments that in conjunction with elevated pressures and an antimicrobial solution uses ultrasonic waves to lyse cell walls.

A need also exists for an apparatus and method of sterilizing instruments that is heat independent.

A need further exists for an apparatus and method for the sterilization of dental and medical instruments at or near room temperature so that the "cold" sterilized instruments can be rinsed, dried off and used immediately after sterilization without having to first cool down the instruments.

SUMMARY OF THE INVENTION

Briefly described, the invention is an apparatus and method for sterilizing instruments, such as dental and medical instruments. Preferably, the instruments are "cold" sterilized, which means that the instruments are sterilized at or near room temperature. More specifically, the apparatus of the present invention generally and, in a preferred embodiment, comprises a container having a lid, which when sealed is air tight and, which can withstand pressures in excess of one atmosphere, such as for example, at least 120 psi without failure. The container and lid are particularly designed and arranged such that the container can contain an antimicrobial solution and so that the lid will provide air space above the level of the antimicrobial solution when the lid is closed to seal the container. In addition, the inside of the container may further comprise a support means, such as a screen, for supporting an instrument submerged in the antimicrobial solution thereon, and for allowing biological matter on said instrument to fall-off of the instrument and pass through the support means to the bottom of the container. The lid of the container must be able to withstand pressures in excess of one atmosphere, such as for example, at least 120 psi. In a preferred embodiment, the lid of the container has an opening therein for allowing pressurized gas to enter into the sealed container to increase the pressure within the container to thereby drive the antimicrobial solution into the cracks and crevices of an instrument. Preferably, the pressurized gas is not substantially dispersed in the antimicrobial solution.

In addition to the container, the apparatus of the present invention further comprises a pressure means that pressurizes a gas to greater than one atmosphere and up to several hundred psi and delivers the pressurized gas through the container lid and into the container. The pressure means increases the pressure in the container, independent of heat, and drives the antimicrobial solution into the cracks and crevices of an instrument. Preferably, the pressure means does not substantially disperse pressurized gas into the antimicrobial solution because bubbles in the antimicrobial solution can occlude areas of an instrument from the antimicrobial solution. Suitable pressure means such as common place air compressors, are well known in the art. For example, an Air Techniques, Incorporated, compressor may be purchased from Atlanta Dental Supply Company as model no. 230-1-60. A flexible hose connects the pressure means and the container lid. The flexible hose can be made of any suitable material, such as plastic, metal, elastomers, textiles, or composites thereof, provided the tube is able to withstand as much pressure as is needed to sterilize an instrument without failure.

The apparatus of the present invention further comprises a vibration means, such as an ultrasonic cleaner, beneath the container. The vibration means vibrates the container and antimicrobial solution and instruments therein to generate waves, including ultrasonic waves, in the solution to remove biological matter from the instrument. As more and more biological material is removed, an increasing number of microbes are directly exposed to the antimicrobial solution until all microbes have been neutralized. In addition, the ultrasonic waves weaken the outer membrane of the microbes, which itself may neutralize the microbe, or make it easier for the antimicrobial solution to penetrate the weakened outer membrane of the microbe.

In an alternative embodiment, the apparatus of the present invention comprises a container as described above. However, rather than having an opening in the container lid, the lid does not have an opening. Instead, an opening is provided on the side of the container below the height of the lid. Connected to the side opening is a flexible tube, as described above, that is also connected to a hydraulic pump which pumps extra antimicrobial solution from a reservoir into the sealed container. In this embodiment, after the lid has been sealed and gas (ambient air) is trapped within the container above the level of the antimicrobial solution, the pump delivers extra antimicrobial solution from the reservoir into the container to increase the pressure within the container to as much pressure as is needed to sterilize an instrument, such as for example 120 psi. In this embodiment, the pump is used to increase pressure within the container, independent of heat, by reducing and compressing the air space provided by the container lid above the original level of the antimicrobial solution. Preferably, the airspace is reduced and compressed such that the compressed air is not substantially dispersed in the antimicrobial solution.

The method of the present invention, in a preferred embodiment, generally includes filing the container with an antimicrobial solution, submerging an instrument in the antimicrobial solution in the container and then closing the container lid to seal the container such that ambient air is trapped within the container. Preferably, the sterilization is done at or near room temperature. Thus, in a preferred embodiment, the antimicrobial solution and the ambient air are maintained at or near room temperature. After the container is sealed, the pressure means delivers pressurized air, also preferably maintained at room temperature, through the flexible tube and into the container through the hole in the lid to pressurize the contents of the container to greater than one atmosphere. As the container is pressurized, the vibration means vibrates the container and its contents. The increased pressure should be maintained for a period of time long enough to sterilize the instrument. Because the sterilization process is conducted at or near room temperature and the instruments are not heated during sterilization, after sterilization, the instruments do not need to be cooled prior to human contact and use. Instead, after sterilization the cold sterilized instruments can be immediately removed from the apparatus, rinsed, dried and used.

In an alternative embodiment, after the container has been sealed extra antimicrobial solution is delivered by the pump from the reservoir through the container side opening and into the container in order to pressurize the contents of the container to greater than one atmosphere and to as much pressure as is needed to sterilize an instrument, such as for example 120 psi. In either embodiment described herein, it is believed that the vibration of the antimicrobial solution inside of the container causes waves in the antimicrobial solution that remove biological matter from the instrument, such as tissue, skin, blood, plaque, food and microbes, so that the contaminating microbes on the instrument and, in particular, in microscopic crevices of the instrument, are exposed to the antimicrobial solution, which neutralizes the microbes. It is also believed that the vibration means itself, by ultrasonic waves, can directly disrupt the outer membrane of the microbe to thereby neutralize the microbe. See J. Bacteril. 126(1): 213–21(1976); C. Clarke, *Antigen of Hemophilus Influenza*, Clin-Allergy 7(1); 41–47(1977); Shimakata et at., *Requirement of Glucose for Mycolic Acid Biosynthetic Activity Localized in the Cell Wall of Bacterionema Malruchotii*, Arch-Boichem. Biophys. 247(2): 302–11(1986). It is further believed that if the ultrasonic waves do not directly neutralize the microbe they will soften the microbes outer membrane such that in combination with the increased pressure the antimicrobial solution can penetrate the outer membrane of the microbe.

A non-exhaustive list of representative antimicrobial solutions that may be used according to the present invention, as described herein, to neutralize various microbes includes glutaraldehyde, chlorine, bleach, hydrogen peroxide, ethyl alcohol, isopropyl alcohol, quaternary ammonium compounds, phenolics, and iodophors. Preferably, the selected antimicrobial is effective at or near room temperature. In addition, various "cocktails," or combinations of more than one antimicrobial can be used as the antimicrobial solution of the present invention.

Various instruments may be sterilized according to the method and apparatus described herein. For example, various medical instruments such as scalpels, currettes, needle holders, bone fries, and/or any medical instrument that is not adversely affected by increased atmospheric pressures may be sterilized according to the invention. In addition, various dental instruments such as explorers, dressing pliers, excavators, perio probes, mirrors, hand pieces and/or any dental instrument that is not adversely affected by increased atmospheric pressures may be sterilized according to the invention described herein. The apparatus and method disclosed herein is particularly suited to sterilized fragile and delicate instruments and heat sensitive instruments. Fragile and delicate instruments are particularly suited because the antimicrobial solution is driven into contact with the serrations, hinges, holes, cracks, crevices and interiors of such instruments by a non-damage causing pressure force. In addition, the present apparatus and method is able to sterilize hard to reach places of such instruments. Heat sensitive instruments and parts thereof, such as dental hand pieces, optical instruments, and instruments having non-metallic parts are also effectively sterilized by the present apparatus and method because the entire sterilization process, and the apparatus therefor, are maintained at or near room temperature.

The gas that is sealed within the container when the container lid is closed, is typically ambient air. In the preferred embodiment, the pressurized gas that is delivered by the pressure means inside of the container can be ambient air, nitrogen and any inert gas, or a combination thereof. Preferably, the gas inside the container should remain above the level of the antimicrobial solution and should not be substantially dispersed therein.

The present invention is not intended to be limited by the particular species and strains of microbes that can be neutralized according to the method and apparatus disclosed herein. It should, however, be appreciated that the term "neutralized" is intended to mean to render the microbe non-infectious.

After the container has been pressurized and the instruments inside the container have been sterilized, prior to opening the container lid the pressure within the container should first be reduced by bleeding the pressure through a release valve. In addition, in the alternative embodiment, when the antimicrobial solution is delivered by the pump from the reservoir into the side of the container, the increased pressure within the container should be reduced by reversing the pump such that antimicrobial solution is pumped from the container to the reservoir. After the pressure has been released, the cold sterilized instruments can be readily removed from the container, rinsed, dried and used. As there is no heat or steam pressure that must be released, the present apparatus and method are believed to be more environmentally safe than heat dependent sterilizers. Heat dependent sterilizers, such as an autoclave, release steam, which may release environmental contaminants into the air.

It is therefore an object of the present invention to provide an apparatus and method for removing biological matter from a contaminated instrument and sterilizing the contaminated instrument, including its microscopic crevices, with an antimicrobial solution by pressure forcing the antimicrobial solution into the cracks and microscopic crevices of the instrument at a pressure of greater than one atmosphere and which is sufficient to sterilize the instrument.

It is also an object of the present invention to provide an apparatus and method for sterilizing a contaminated instrument wherein the outer membrane of the microbe contaminating the instrument is disrupted and/or softened by ultrasonic waves such that the microbe is either neutralized and/or the microbe is more accessible and penetrable to an antimicrobial solution.

It is a further object of the present invention to provide an apparatus and method for sterilizing a microbe contaminated instrument by using a pressure force of greater than one atmosphere to drive an antimicrobial solution into the outer membrane of a microbe to thereby neutralize the microbe.

It is also an object of the present invention to provide an apparatus and method for the cold sterilization of contaminated instruments that does not heat the instruments to be sterilized.

It is an additional object of the present invention to provide an apparatus and method for sterilizing contaminated instruments that is cost effective, small and quiet enough to be located in any particular room in which a medical or dental procedure is conducted.

Other objects, features and advantages of the present invention will become apparent from the following description when read in conjunction with the accompanying drawings.

DETAILED DESCRIPTION OF THE INVENTION

Figure 1:
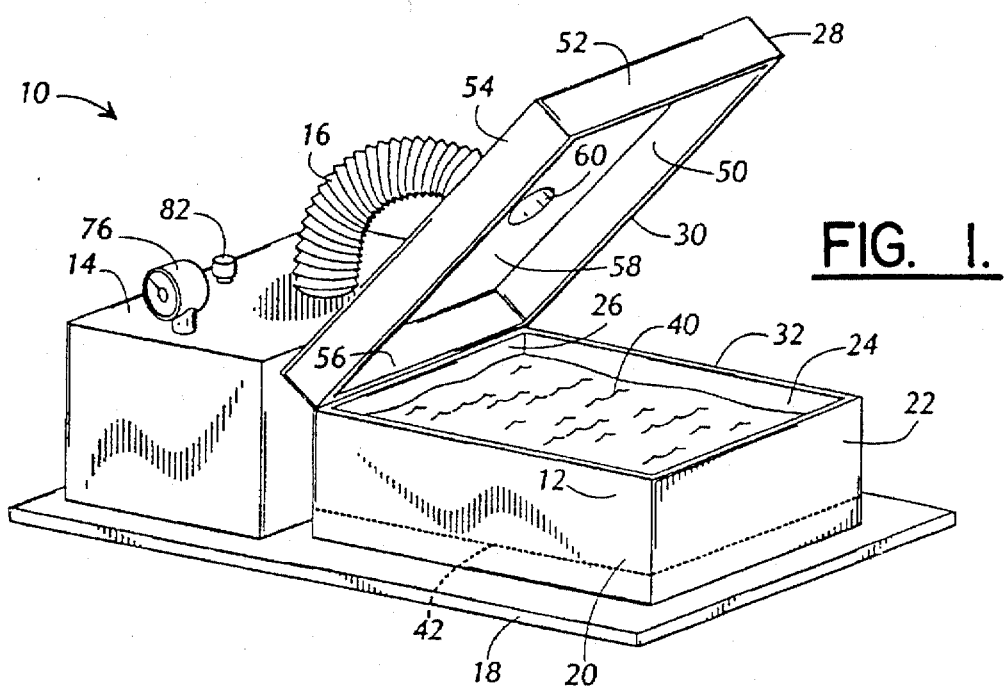
FIG. 1 is a perspective view of a preferred embodiment of the apparatus for sterilizing contaminated instruments.
Figure 2:
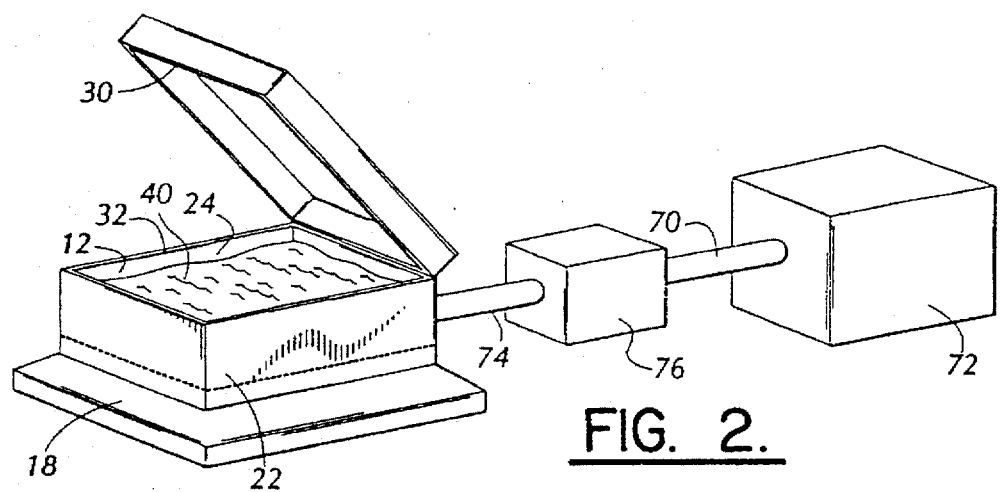
FIG. 2 is a perspective view of an alternative embodiment of the present invention.
Figure 3:
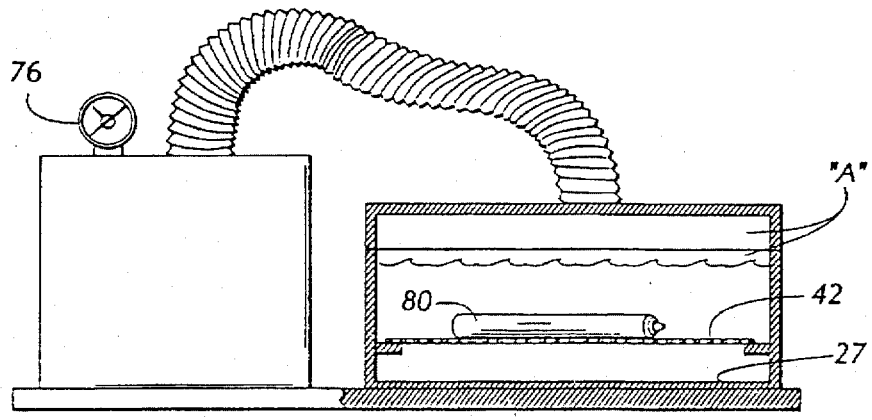
FIG. 3 is a cut side view of a preferred embodiment of the apparatus for sterilizing contaminated instruments.

Referring now in detail to the drawings in which like numbers refer to the same structure throughout the figures, a preferred embodiment of the apparatus of the present invention is generally referred to as reference number 10. Sterilization apparatus 10 comprises receptacle 12, pressure means 14, pressure hose 16, and vibration means 18. More specifically, receptacle 12 is generally a rectangularly shaped box having side walls 20, 22, 24 and 26 and a bottom 27. In addition, receptacle 12 further comprises a lid 28, which has an open position (FIG. 1) and a closed position (FIG. 3). Lid 28 comprises sides 50, 52, 54 and 56 and top 58. In a preferred embodiment top 58 further comprises opening 60.

Lid 28 and receptacle 12 are provided with seals 30 and 32, respectively. When lid 28 is in its closed position (FIG. 3), receptacle 12 and lid 28 are sealed air tight by seals 30 and 32. Receptacle 12, lid 28 and seals 30 and 32 are therefore all constructed of materials which can withstand as much pressure as is necessary to sterilize instrument 80 without failure. Receptacle 12 is also liquid impervious such that it can contain antimicrobial liquid 40 without leakage. Therefore, receptacle 12 receives, houses and contains antimicrobial liquid 40. In a preferred embodiment, grid shelf 42 is positioned inside of receptacle 12. Instrument 80 can be placed on grid shelf 42 such that debris can fall off of instrument 80, through grid shelf 42, and to bottom 27 of receptacle 12.

Connected to lid 28, and in particular lid opening 60, is a flexible pressure hose 16. Pressure hose 16 is also connected to pressure means 14 such that as air pressure is created by pressure means 14, pressure hose 16 can deliver the generated air pressure inside of lid 28 and receptacle 12 when lid 28 is in its closed position.

Air pressure means 14 can be any of several well known air compressors. For example, an Air Techniques, Incorporated, compressor is suitable for the purposes of this invention. However, the air pressure means should be capable of producing greater than one atmosphere of pressure, preferably several hundred psi, inside of receptacle 12 when lid 28 is in its closed position. Preferably, air pressure means 14 generates air pressure independent of heat.

Positioned below receptacle 12 is vibration means 18. Vibration means 18 is preferably an ultra-sonic cleaner that is able to vibrate receptacle 12 such that antimicrobial solution 40, which is inside of receptacle 12, is also vibrated to thereby cause agitation of antimicrobial solution 40. It is believed that vibration means 18 causes ultra-sonic waves in antimicrobial solution 40 which disturb and/or disrupt the outer membrane of the microbes contaminating instrument 80.

In the operation of the preferred embodiment, receptacle 12 is first filled with antimicrobial solution 40 at a level that is high enough to submerge instrument 80, but also at a level that is low enough such that it will not spill over side walls 20, 22, 24 and 26. Instrument 80, is then placed within receptacle 12 such that it is completely submerged in antimicrobial solution 40. Preferably, antimicrobial solution 40 is at or near room temperature. Instrument 80 can either be placed on bottom 27 or it can be placed on support shelf 42. Thereafter, lid 28 is closed such that receptacle 12 and lid 28 are sealed air tight by seals 30 and 32. Lid 28 must ensure that air is trapped within sealed receptacle 12 above the level of antimicrobial solution 40. Preferably, the air trapped within sealed receptacle 12 is at or near room temperature. After lid 28 has been sealed, vibration means 18 is activated to agitate the contents of sealed receptacle 12. In addition, after lid 28 has been closed to air tight seal receptacle 12, pressure means 14 is activated to generate air pressure and deliver the generated air pressure through pressure hose 16 and lid opening 60 into sealed receptacle 12. The air pressure within the sealed receptacle 12 is preferably generated independent of heat and is generated to a pressure that is above normal atmospheric pressure and up to 120 psi, or greater if necessary. After the desired amount of pressure has been achieved within sealed receptacle 12, the desired amount of pressure is maintained within the sealed receptacle 12 for a time period sufficient to sterilize the instrument contained therein. It is desired that such time period could be as low as one (1) minute, however, depending upon the particular instrument to be sterilized, the particular microbes contaminating the instrument, and the amount of pressure, the amount of time may vary. Generally, when the pressure is approximately 100–120 psi, the pressure is maintained for approximately three (3) minutes. After the necessary amount of time has expired, pressure release valve 82 on pressure means 14 is operated to decrease the pressure within sealed receptacle 12. Thereafter, lid 28 is opened and instrument 80 is removed from receptacle 12, rinsed and dried.

In an alternative embodiment, reservoir 72, which contains excess antimicrobial solution 40, is connected to pump means 76 by reservoir hose 70. Pump means 76 is connected to receptacle 12 by pump hose 74, such that pump hose 74, pump means 76, and reservoir hose 70, allow antimicrobial solution to pass to and from reservoir 72 and receptacle 12. In this embodiment, to sterilize an instrument, instrument 80 is first placed inside of receptacle 12, either on bottom 27, or on support shelf 42. However, instrument 80 needs to be put into receptacle 12 such that instrument 80 is totally submerged in antimicrobial solution 40, which preferably is at or near room temperature. After instrument 80 has been submerged in antimicrobial solution 40, lid 28 is closed such that seals 30 and 32 render the closed receptacle 12 and lid 28 air tight such that air space "A" is created above antimicrobial solution 40. Preferably, the air in air space "A" is at or near room temperature. After lid 28 has been closed, vibration means 18 is activated such that the contents of receptacle 12 are agitated. In addition, after receptacle 12 and lid 28 have been sealed, pump means 76 is activated such that it delivers antimicrobial solution 40 from reservoir 72 through reservoir hose 70, pump means 76, pump hose 74, and into receptacle 12. As increasing amounts of antimicrobial solution 40 are delivered into receptacle 12, the air originally trapped inside of lid 28 (air space "A"), is pressurized, independent of heat, such that a pressure force of greater than one atmosphere and which is sufficient to sterilize instrument 80 is produced within sealed receptacle 12 and lid 28.

The pressure generated within the sealed receptacle 12 should be maintained for as much time as is necessary to sterilize instrument 40, which is of course dependent upon the mount of pressure, the type of instrument, and the microbe contaminating the instrument. However, when the pressure is approximately 100–120 psi, the pressure should be maintained for approximately three (3) minutes to sterilize the instrument. After the sterilization time has elapsed for sterilizing the instrument, the pressure within the sealed receptacle 12 is reduced by reversing pump means 76 such that antimicrobial solution 40 is pumped out of receptacle 12 and into reservoir 72. Lid 28 is thereafter opened and the instrument contained within receptacle 12 is removed and dried if necessary.

Regardless of the particular embodiment of the present invention that is employed to sterilize microbially contaminated instruments, it is believed that the combination of the pressure force and the vibration, attenuate, disrupt, or force the antimicrobial solution to penetrate the outer membrane of a microbe that is on the contaminated instrument. In addition, it is believed that the generated pressure forces the antimicrobial solution into the cracks and microscopic crevices of an instrument that the antimicrobial solution might not otherwise contact, such that the antimicrobial solution contacts and decontaminates the entirety of the contaminated instrument. It is further believed that vibration means 18 transmits ultrasonic waves within antimicrobial solution 40 that acts upon the outer membrane of a microbe to attenuate, disrupt, or destroy the outer membrane of a microbe to thereby neutralize the microbe and sterilize the instrument.

Although the forgoing invention has been described by way of illustration and example for purposes of clarity and understanding, it will be apparent to those skilled in the art that numerous changes or modifications may be made thereto without the departure from the spirit and scope of the invention as claimed hereinafter.

I claim:

1. A method for sterilizing a microbially contaminated instrument independent of heat, comprising:

containing an antimicrobial solution at room temperature in a container having a lid;

submerging a microbially contaminated instrument having a microscopic crevice in said antimicrobial solution;

closing said lid such that a gas is trapped within said container above said antimicrobial solution;

introducing a room temperature pressurized gas above said antimicrobial solution to pressurize said antimicrobial solution without substantially dispersing said pressurized gas into said antimicrobial solution such that said antimicrobial solution penetrates the crevices of said instrument; and vibrating said sealed container to remove biological matter from said instrument, whereby the pressurization and vibration of said antimicrobial solution forces said antimicrobial solution into contact with the microbes on said microbially contaminated instrument to thereby sterilize said instrument.

2. The method of claim 1, wherein said step of vibrating said sealed container causes ultrasonic waves in said antimicrobial solution that weakens the cell wall of the microbe contaminating said instrument.

3. The method of claim 2, wherein said step of introducing a pressurized gas above said antimicrobial solution forces said antimicrobial solution into the weakened cell wall of the microbe contaminating said instrument.

4. The method of claim 1, wherein said instrument is a dental instrument that is not adversely affected by pressures in excess of one atmosphere.

5. The method of claim 1, wherein said instrument is a medical instrument that is not adversely affected by pressures in excess of one atmosphere.

6. The method of claim 1, wherein said antimicrobial solution is selected from the group consisting of glutaraldehyde, hydrogen peroxide, ethyl alcohol, isopropyl alcohol, quaternary ammonium compounds, iodophors, phenolics, bleach, and DMSO.

7. The method of claim 1, wherein said gas is selected from the group consisting of ambient air, nitrogen and inert gas.

8. The method of claim 1, wherein said container can withstand pressures greater than one atmosphere.

9. A method for sterilizing a microbially contaminated instrument independent of heat, comprising:

containing an antimicrobial solution at room temperature in a container having a lid;

submerging an instrument contaminated with a microbe having an outer membrane in said antimicrobial solution;

closing said lid such that a gas is trapped within said container above said antimicrobial solution, introducing additional antimicrobial solution to reduce and compress said trapped gas without substantially dispersing said compressed gas into said antimicrobial solution such that said antimicrobial solution is forced into said crevices of said instrument such that said antimicrobial solution attenuates the outer membrane of said microbe to thereby sterilize said instrument; and vibrating said sealed container to remove biological matter from said instrument, whereby the pressurization and vibration of said antimicrobial solution force said antimicrobial solution into contact with the microbes on said microbially contaminated instrument to thereby sterilize said instrument.

10. The method of claim 9, wherein said antimicrobial solution is selected from the group consisting of glutaraldehyde, hydrogen peroxide, ethyl alcohol, isopropyl alcohol, quaternary ammonium compounds, iodophors, phenolics, bleach, and DMSO.

11. The method of claim 9, wherein said microbe is selected from the group consisting of bacteria, spores, fungi and viruses.

12. The method of claim 9, wherein said container can withstand pressures greater than one atmosphere.

* * * * *